(12) United States Patent
Rossner et al.

(10) Patent No.: US 7,706,683 B2
(45) Date of Patent: Apr. 27, 2010

(54) SELF ADJUSTING OPERATION LAMP SYSTEM

(75) Inventors: Holger-Claus Rossner, Feldkirchen (DE); Günter Goldbach, Forstinning (DE)

(73) Assignee: BrainLAB AG, Feldkirchen (DE)

( * ) Notice: Subject to any disclaimer, the term of this patent is extended or adjusted under 35 U.S.C. 154(b) by 694 days.

(21) Appl. No.: 11/421,201

(22) Filed: May 31, 2006

(65) Prior Publication Data

US 2007/0014567 A1 Jan. 18, 2007

Related U.S. Application Data

(60) Provisional application No. 60/688,669, filed on Jun. 8, 2005.

(30) Foreign Application Priority Data

May 31, 2005 (EP) .................................. 05011682

(51) Int. Cl.
*G03B 17/48* (2006.01)
(52) U.S. Cl. .................................. 396/429; 396/431
(58) Field of Classification Search ................ 396/429, 396/14, 431; 362/33, 362, 370, 371, 372, 362/382, 249, 250, 418, 419, 458; 352/362, 352/370, 371, 372, 382; 600/178–180, 247–249
See application file for complete search history.

(56) References Cited

U.S. PATENT DOCUMENTS

| | | | |
|---|---|---|---|
| 4,578,575 A | 3/1986 | Roos | 250/203 |
| 4,639,838 A | 1/1987 | Kato et al. | 362/33 |
| 5,038,261 A | 8/1991 | Kloos | 362/286 |
| 5,347,431 A * | 9/1994 | Blackwell et al. | 362/11 |
| 5,383,105 A | 1/1995 | Agut | 362/285 |
| 6,160,582 A * | 12/2000 | Hill | 348/370 |
| 6,434,329 B1 | 8/2002 | Dube et al. | 396/14 |
| 6,471,363 B1 * | 10/2002 | Howell et al. | 362/11 |
| 6,639,623 B2 * | 10/2003 | Howell et al. | 348/61 |
| 2003/0021107 A1 * | 1/2003 | Howell et al. | 362/147 |
| 2003/0153978 A1 | 8/2003 | Whiteside | 623/20.21 |
| 2003/0164953 A1 * | 9/2003 | Bauch et al. | 356/611 |
| 2003/0210812 A1 | 11/2003 | Khamene et al. | 382/128 |
| 2005/0195587 A1 * | 9/2005 | Moctezuma De La Barrera et al. | 362/5 |

FOREIGN PATENT DOCUMENTS

| | | |
|---|---|---|
| DE | 102 46 147 A1 | 4/2004 |
| EP | 0 421 130 A2 | 9/1990 |
| EP | 0 421 130 B1 | 6/1994 |
| EP | 1 340 470 A1 | 3/2002 |
| WO | 2004/030560 A2 | 4/2004 |

* cited by examiner

*Primary Examiner*—Melissa J Koval
*Assistant Examiner*—Warren K Fenwick
(74) *Attorney, Agent, or Firm*—Renner, Otto, Boisselle & Sklar, LLP

(57) ABSTRACT

A combined operation lamp image detecting system includes an operation lamp attached to a movable mount, and at least one camera arranged in a fixed, known and/or detectable positional relationship relative to the operation lamp. The moveable mount includes actuators that are controlled on the basis of image signals detected by the camera so as to maintain shadow free illumination of a workspace.

24 Claims, 1 Drawing Sheet

SELF ADJUSTING OPERATION LAMP SYSTEM

RELATED APPLICATION DATA

This application claims priority of U.S. Provisional Application No. 60/688,669 filed on Jun. 8, 2005, which is incorporated herein by reference in its entirety.

FIELD OF THE INVENTION

The invention relates to operation lamps and, more particularly, to a combined operation lamp image detecting system and a method for operating such a system.

BACKGROUND OF THE INVENTION

Operation lamps provide illumination of a medical workspace and, as will be appreciated, generally are oriented so as to minimize the formation of shadows in the medical workspace. EP 1 340 470 B1 discloses a conventional illumination system that includes an operation lamp attached to a moveable mount, and at least one camera arranged in a fixed, known and/or detectable positional relationship relative to the operation lamp.

In some situations, maintaining a shadow-free environment of the medical workspace may be difficult using conventional operation lamps, particularly if the surgeon comes between the lamps and the patient. In such cases, the operation lamp is manually adjusted and/or rearranged so as to achieve an optimal illumination of the medical workspace.

SUMMARY OF THE INVENTION

A combined operation lamp and image detecting system includes a moveable mount having movement devices that can be controlled on the basis of image signals detected by a camera. In other words, the image content captured by camera (i.e., the camera image) may be linked to the positioning of the operation lamp, such that the position of the lamp can be adjusted so as to achieve a shadow-free and/or optimal illumination of the medical workspace (also referred to as the operation field). If it can be inferred from the image content that the illumination is no longer optimal (e.g., if instruments that should be present in the operation field disappear from the camera image), the operation lamp's position can be automatically and autonomously readjusted until the instruments and, therefore the operation field, are again within the field of view of the camera (and thus illuminated by the operation lamp). This is possible because the camera and operation lamp are directed onto substantially the same field of view.

Data transfer devices can be provided for transferring data between the movement devices and the camera. The system also can include a control/regulating unit integrated into data transfer, in particular a medical navigation system, wherein the navigation system advantageously forms or includes the control/regulating unit for controlling/regulating the movement devices. In principle, however, a separate control/regulating unit also can be provided without a navigation system or in addition to the navigation system. The data transfer devices, for example, can be data transfer cables or wireless data transfer devices that include transmitters and receivers.

The camera can be arranged centrally in the operation lamp housing. Further, the camera can be provided with a housing that also serves as a shaft for a sterile holding grip of the operation lamp.

The system can include a light source for emitting light in a delimited spectral range, in particular an infrared light source. This light source can be controllable together with the camera or can directly control the camera. Preferably, the camera is operative to detect light in the aforesaid spectral range, and is provided with a filter that is permeable to light in said range.

The system also can include a number of cameras that may be used together, individually and/or alternately. It is also possible to assign the system an instrument or set of instruments that are clearly identifiable by the navigation system, in particular known to and/or stored in the navigation system on the basis of a characteristic reference array. Instruments also can be identified by way of contour recognition (external contour of instruments), for example. Advantageously, using such instruments that are "known to the system", it is possible to track corresponding reference arrays using the camera and also to determine if the reference arrays have left the camera's field of view and, therefore, also has left the field of optimal illumination. If it is determined that the reference arrays are not within the field of view, then the light source can be automatically repositioned so as to change the illumination.

A method for operating a combined operation lamp image detecting system includes controlling/regulating the moveable mount by means of controllable movement devices on the basis of signals from the camera. The signals can be used to move the operation lamp image detecting system to a desired position. Here again, the possibility exists of providing a separate control/regulating unit or one integrated into a navigation system, and of incorporating the control/regulating unit into data transfer. In accordance with one embodiment, a light source for light in a delimited spectral range, in particular an infrared light source, also can be controllable and/or controlled together with the camera, wherein the camera can be designed for detecting light in this spectral range. Preferably, the camera is provided with a filter that is permeable to light in said range, and wherein the operation lamp is aligned with the aid of the light reflections.

The operation lamp image detecting system can comprise only a single camera or a number of cameras, wherein at least one camera, which can be used individually or in combination with the other cameras, captures image data that can be evaluated to establish whether the field of view of one of the cameras is restricted. If a camera's field of view is found to be restricted, another camera or a number of other cameras whose field of view is not restricted can be used. The light sources then can be controlled individually by or using the individual cameras, and can be arranged on individual mounts (e.g., holding arms). When a number of cameras are used, it is possible to compare and/or match image signals and to determine mismatches and, based on this information, take appropriate correction measures.

In accordance with another embodiment, the camera can be used to track instruments, wherein an instrument or set of instruments that are clearly identifiable by the navigation system (e.g., known to or stored in the navigation system on the basis of a characteristic reference array) is/are positionally detected. Another way of evaluating the image signal is to change the focus or illumination field of the operation lamp on the basis of the image signals captured by the camera.

The invention also includes a combined operation lamp image detecting system comprising an operation lamp attached to a mount, and a camera that is arranged in a fixed, known and/or detectable positional relationship relative to the operation lamp. The camera may be the only camera in the system and may be operable to detect positions in three-dimensional space. In this environment, all of the system features outlined above can be realized. The invention also includes a method for operating the combined operation lamp image detecting system.

BRIEF DESCRIPTION OF THE DRAWINGS

The forgoing and other embodiments of the invention are hereinafter discussed with reference to the drawings.

DETAILED DESCRIPTION

Figure 1:
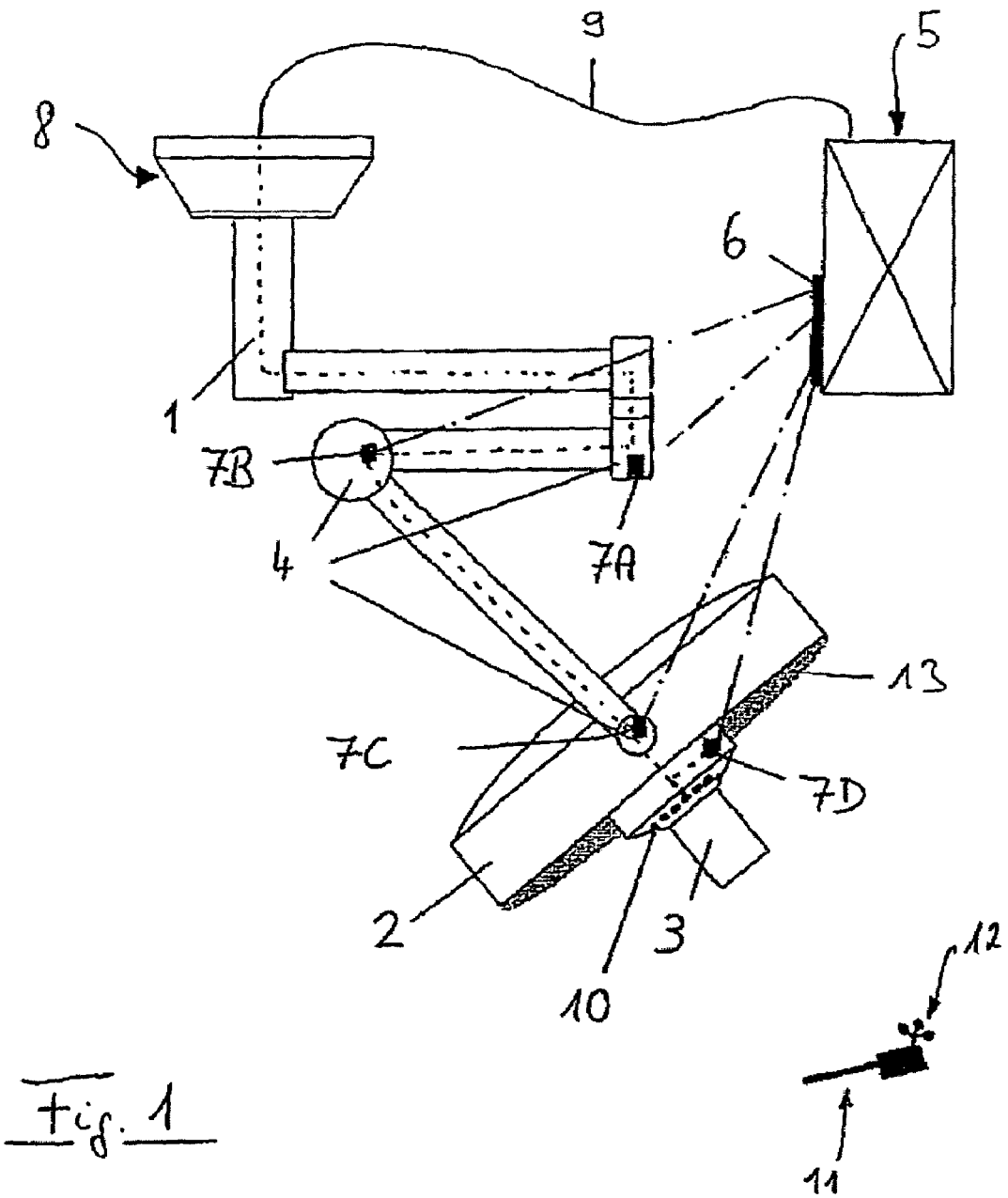
FIG. 1 is a schematic representation of an exemplary combined operation lamp image detecting system in accordance with the invention.

FIG. 1 shows an operation lamp 2 attached to a ceiling attachment 8 via a moveable mount 1. The moveable mount 1 includes a number of arms that are jointed together, wherein the lamp 2 is jointed to the last arm. In the joints, movement devices are provided (e.g., actuators such as rotational servo-motors or the like) and are indicated by a single reference sign 4. With the aid of the rotational servo-motors or servos 4 in the joints, the lamp 2 can be moved on the arms to any desired position. The operation lamp 2 can have movement devices in one or more axes and/or may be adjusted only at the last gimbal-mounted member.

It should be noted that the movement devices do not necessarily have to be rotational servo-motors. Any known movement devices can be used, including elongation devices such as, for example, telescoping systems.

The lamp 2 comprises illumination means 13 for illuminating the operation field. The illumination means 13 centrally supports a camera 3 that is operable to detect optical image signals, and infrared LEDs 10 are arranged on the camera 3. The lamp Illumination also can be used as the navigation light. FIG. 1 also schematically shows a surgical instrument 11 in front of the camera, said instrument 11 supporting a reference array 12 comprising three infrared light reflectors. Alternatively, active elements (e.g., LEDs), which may be referred to as active emitter reference arrays, can be used in place of or in conjunction with the reflectors.

FIG. 1 shows two possible systems for transferring data between a control/regulating unit 5 and the other system parts (rotational servos 4, camera 3). These two data transfer systems need not co-exist; they can be used individually and independently of each other. The control/regulating unit 5 is essentially an integrated circuit or a computer for signal processing, and may be a medical navigation system and/or a medical tracking system, as is for example described in DE 19 639 615 A1, the contents of which is hereby incorporated by reference in its entirety. The unit 5 also can be a data processing part of said navigation system.

One form of data transfer as shown is based on a cable connection 9 which electrically and/or optically connects the unit 5 to the servo-motors 4, the camera 3 and the LED array 10. The second form of data transfer relates to cable-free or wireless data transfer, wherein a transmitter/receiver 6 is arranged on the control/regulating unit 5. This transmitter/receiver 6 communicates with other transmitters/receivers 7A, 7B, 7C (on the servo-motors 4) and 7D (for the camera 3 and the infrared LEDs 10).

The transmitters/receivers 6 and 7 (7A to 7D) serve to transfer data between the unit 5 and the other systems. In particular, movement commands may be output from the unit 5 to the servos 4, and on/off commands may be output to the camera 3 and the LED array 10. Additionally, the servos 4 can convey positional feedback to the unit 5, and the camera 3 can transfer images to the unit 5 for processing.

When in use, the system can be used, for example, for the shadow-free illumination of an area (operation field). The camera can provide two-dimensional or three-dimensional images that in combination with the unit 5, for example, may be used to control and/or regulate the position of the lamp 2 and/or to track the surgical instrument 11. This utilizes the fact that a particular instrument 11 having a clearly identifiable reference array 12 or contour (which is known to the navigation system 5) is situated in the operation field during the operation. If light is intermittently or continually emitted by the infrared LEDs 10, this light is then reflected by the marker array 12, and the camera 3 can detect this reflection. On the basis of this detected data, it is then possible to determine whether the operation lamp 2 is situated at the optimal location and/or is optimally adjusted, since the corresponding image data are transferred to the control/regulating unit 5 (navigation system) where they are evaluated. If it is determined that the lamp 2 is no longer in an optimal position, the unit 5 can issue readjustment commands to the servo-motors 4 which then move the lamp 2 such that the instrument is once again in an optimal position. As a result, the lamp 2 is optimally illuminating the operation field without shadows.

In a simple regulation scheme, for example, it may be determined that the marker array 12 is or has been removed from the camera's field of view (e.g., repeatedly and/or in a particular direction over a predetermined period of time) or the marker array is always concealed in one direction. This direction could be determined by evaluating the camera image within the unit 5 and, based on the evaluation, calculating a desired counter movement of the lamp 2. The lamp 2 then can be repositioned by controlling the servo-motors 4. As a result of the movement, the camera again has an optimal line of sight, which also means that the operation field is optimally illuminated.

The camera can simultaneously be used to identify and/or track instruments (i.e., positionally locate and track), such as the schematically shown instrument 11, on the basis of the marker array 12. This is possible with a single camera if the instruments are clearly identifiable and their shape and/or characteristic marker arrays are stored in a memory of the navigation system 5. A number of cameras can also be used, which in addition to the tracking and lamp positioning functions can also fulfil redundant functions, in order to eliminate obstructions to the view or differences in the image content.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A combined operation lamp image detecting system for use in a medical workspace, comprising:
   an operation lamp attached to a movable mount;
   an emitter configured to emit light in the non-visible spectrum;
   at least one camera arranged in a fixed, known and/or detectable positional relationship relative to the operation lamp, the at least one camera operable to detect non-visible light emitted by the emitter;
   at least one actuator operatively coupled to the movable mount for effecting a change in position of the operation lamp; and
   a controller operatively coupled to the actuator and the at least one camera, wherein the controller receives image signals of the medical workspace from the at least one camera and based on the image signals, commands the actuator to adjust a position of the operation lamp so as to maintain shadow free illumination of the medical workspace.

2. The system according to claim 1, further comprising data transfer devices operable to transfer data between the actuators and the camera.

3. The system according to claim 2, wherein the data transfer devices include wireless data transfer devices.

4. The system according to claim 2, further comprising a control/regulating unit for directing the data transfer.

5. The system according to claim 4, wherein the control/regulating unit is a medical navigation system.

6. The system according claim 5, further comprising at least one instrument identifiable by the navigation system.

7. The system according to claim 6, wherein said instrument is known to and/or stored in the navigation system on the basis of a characteristic reference array.

8. The system according to claim 1, wherein the camera is arranged centrally in the operation lamp housing.

9. The system according to claim 1, wherein the camera comprises a housing that serves as a shaft for a sterile holding grip of the operation lamp.

10. The system according to claim 1, wherein the at least one camera includes a plurality of cameras that are operable to be used together, individually and/or alternately.

11. The system according to claim 1, wherein the emitter is arranged on the at least one camera.

12. A combined operation lamp image detecting system for use in a medical workspace, comprising:
    an operation lamp attached to a movable mount;
    at least one camera arranged in a fixed, known and/or detectable positional relationship relative to the operation lamp;
    at least one actuator operatively coupled to the movable mount for effecting a change in position of the operation lamp; and
    a controller operatively coupled to the actuator and the at least one camera, wherein the controller receives image signals of the medical workspace from the at least one camera and based on the image signals, commands the actuator to adjust a position of the operation lamp so as to maintain shadow free illumination of the medical workspace, wherein the camera is operable to detect positions in three-dimensional space of an object.

13. A method for operating a combined operation lamp image detecting system including an operation lamp which is attached to a movable mount, and at least one camera which is arranged in a fixed, known and/or detectable positional relationship relative to the operation lamp, comprising:
    collecting image data of a medical workspace;
    determining from the image data if the medical workspace is receiving shadow-free illumination; and
    based on the determination, automatically adjusting a position of the operation lamp to provide shadow free illumination of the medical workspace.

14. The method according to claim 13, wherein the camera comprises a plurality of cameras arranged in a fixed, known and/or detectable positional relationship relative to the operation lamp, comprising evaluating signals from at least two cameras of the plurality of cameras to determine whether the field of view of one of the two cameras is restricted.

15. The method according to claim 14, wherein if a camera field of view is restricted, then using another camera of the plurality of cameras whose field of view is not restricted.

16. The method according to claim 15, further comprising arranging a plurality of light sources on individual mounts, wherein said light sources can be individually controlled by the individual cameras.

17. The method according to claim 15, wherein the cameras are used to match the image signals and to determine mismatches.

18. The method according to claim 13, further comprising:
    using a light source to emit light in a delimited spectral range;
    controlling a position of the light source together with a position of the cameras, said cameras operable to detect light in the delimited spectral range; and
    aligning the operation lamp based on data captured by the camera.

19. The method according to claim 18, wherein controlling a position includes controlling actuators coupled to the moveable mount based on signals from the camera so as to move the operation lamp image detecting system to a desired position.

20. The method according to claim 19, wherein data are transferred between the actuators and the camera via a control/regulating unit.

21. The method according to claim 13, further comprising using the camera to positionally track an instrument.

22. The method according to claim 13, further comprising changing the focus or illumination field of the operation lamp on the basis of the image signals captured by the camera.

23. A method for operating a combined operation lamp image detecting system comprising an operation lamp attached to a mount, and at least one camera arranged in a fixed, known and/or detectable positional relationship relative to the operation lamp, comprising:
    using the camera to detect a position in three dimensional space of an instrument; and
    altering a relative position of the camera together with the operation lamp based on the detected spatial position of the instrument.

24. The method according to claim 23, further comprising controlling a moveable mount via actuators based on signals from the camera so as to move the operation lamp image detecting system to a desired position.

* * * * *